(12) United States Patent
Miyazawa et al.

(10) Patent No.: US 10,363,574 B2
(45) Date of Patent: Jul. 30, 2019

(54) PIEZOELECTRIC ELEMENT, PROBE, AND ULTRASONIC MEASUREMENT APPARATUS

(71) Applicant: SEIKO EPSON CORPORATION, Tokyo (JP)

(72) Inventors: Hiromu Miyazawa, Azumino (JP); Hiroshi Ito, Suwa (JP); Tomoaki Nakamura, Chino (JP); Masayoshi Yamada, Chino (JP); Jiro Tsuruno, Okaya (JP); Tsukasa Funasaka, Shiojiri (JP)

(73) Assignee: SEIKO EPSON CORPORATION, Tokyo (JP)

( * ) Notice: Subject to any disclaimer, the term of this patent is extended or adjusted under 35 U.S.C. 154(b) by 375 days.

(21) Appl. No.: 15/283,367

(22) Filed: Oct. 1, 2016

(65) Prior Publication Data

US 2017/0095837 A1   Apr. 6, 2017

(30) Foreign Application Priority Data

Oct. 2, 2015   (JP) .................................. 2015-196762

(51) Int. Cl.
| | | |
|---|---|---|
| *H01L 41/09* | (2006.01) | |
| *H01L 41/047* | (2006.01) | |
| *B06B 1/06* | (2006.01) | |
| *A61B 8/00* | (2006.01) | |
| *G01N 29/24* | (2006.01) | |

(52) U.S. Cl.
CPC .......... *B06B 1/0603* (2013.01); *A61B 8/4444* (2013.01); *A61B 8/4494* (2013.01); *B06B 1/0622* (2013.01); *G01N 29/2437* (2013.01)

(58) Field of Classification Search
CPC ................ B06B 1/0603; B06B 1/0622; G01N 29/2437; A61B 8/4444; A61B 8/4494
USPC .................................. 310/324, 365, 367, 368
See application file for complete search history.

(56) References Cited

U.S. PATENT DOCUMENTS

| | | | |
|---|---|---|---|
| 5,233,259 A * | 8/1993 | Krishnaswamy | ........ H03H 9/17 |
| | | | 310/322 |
| 6,515,402 B2 | 2/2003 | Klee et al. | |
| 7,224,105 B2 * | 5/2007 | Onishi | ............... H03H 9/02094 |
| | | | 310/320 |
| 9,269,884 B2 | 2/2016 | Nakamura et al. | |
| 2006/0262167 A1 * | 11/2006 | Sugahara | ............. B41J 2/14233 |
| | | | 347/70 |
| 2008/0239018 A1 * | 10/2008 | Sekiguchi | ............ B41J 2/14233 |
| | | | 347/70 |
| 2015/0273526 A1 | 10/2015 | Tsuruno et al. | |

FOREIGN PATENT DOCUMENTS

| | | |
|---|---|---|
| JP | 2002-271897 A | 9/2002 |
| JP | 2013-243512 A | 12/2013 |
| JP | 2010-147658 A | 2/2014 |
| JP | 2015-195351 A | 11/2015 |

* cited by examiner

*Primary Examiner* — Thomas M Dougherty
(74) *Attorney, Agent, or Firm* — Maschoff Brennan

(57) ABSTRACT

A piezoelectric element which includes a vibrating film, a piezoelectric body disposed on one surface of the vibrating film, and a horizontal electrode structure in which electrodes are disposed at a predetermined gap therebetween on the piezoelectric body. The vibrating film includes a recess portion in a portion corresponding to the predetermined gap in plan view.

20 Claims, 15 Drawing Sheets

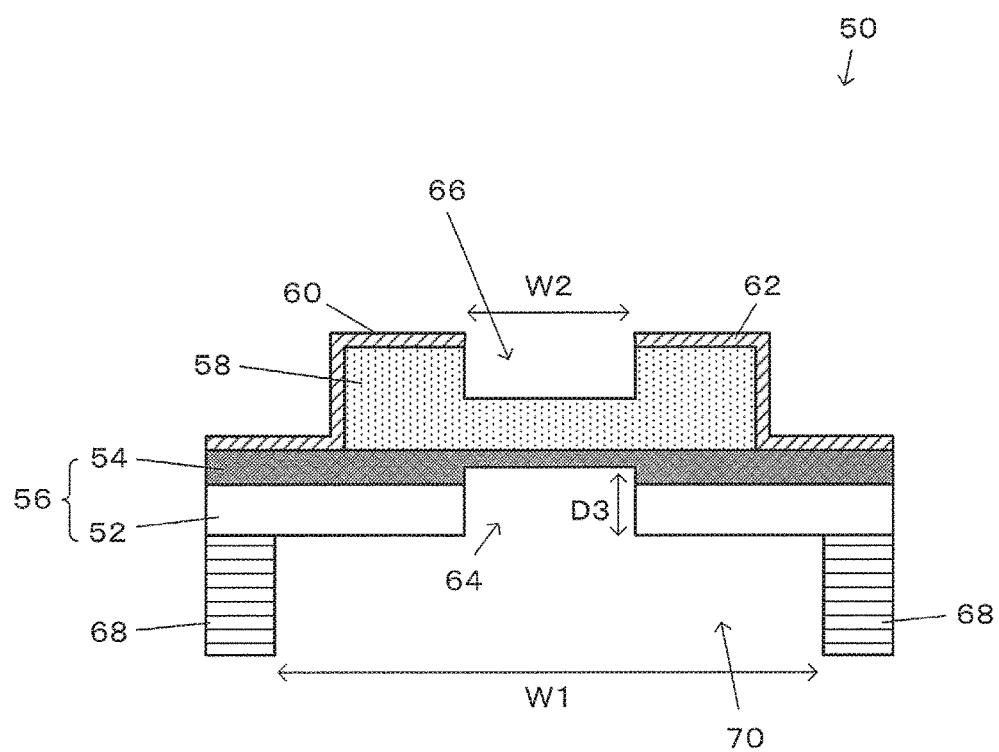
FIG. 6
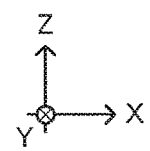

PIEZOELECTRIC ELEMENT, PROBE, AND ULTRASONIC MEASUREMENT APPARATUS

PRIORITY INFORMATION

The present invention claims priority to Japanese Patent Application No. 2015-196762 filed Oct. 2, 2015, which is incorporated herein by reference in its entirety.

BACKGROUND

1. Technical Field

The present invention relates to a piezoelectric element having a horizontal electrode structure or the like.

2. Related Art

Piezoelectric elements, such as ultrasonic transducers for performing conversion between an ultrasonic wave and an electrical signal are known in the art, including piezoelectric elements having a vertical electrode structure in which electrodes are provided on the upper and lower surfaces of the piezoelectric body. One example of such piezoelectric elements is found in Japanese Patent Document No. JP-A-2002-271897. The principle of a piezoelectric element that receives an ultrasonic wave to generate an electrical signal is that the piezoelectric body having received an elastic wave of an ultrasonic wave is distorted, surface charges are generated due to the distortion, and a potential difference (voltage) occurs between two electrodes.

As the structure of the piezoelectric body, not only the vertical electrode structure but also a horizontal electrode structure is known, in which two electrodes are provided on the one side surface of the piezoelectric body. A piezoelectric element having a horizontal electrode structure has an advantage that reception sensitivity is good compared with the piezoelectric element having a vertical electrode structure.

For example, a piezoelectric element is used in an ultrasonic measurement apparatus that measures biological information by irradiating the human body with ultrasonic waves and receiving the reflected waves. In the ultrasonic measurement apparatus, as the irradiation intensity of the ultrasonic wave becomes higher, the reception intensity becomes higher. Accordingly, more accurate biological information is obtained. However, in order to minimize the influence on the human body, the irradiation intensity needs to be as low as possible. For this reason, there is a need for further improvements in the reception sensitivity in a piezoelectric element that receives reflected waves of ultrasonic waves.

SUMMARY

An advantage of some aspects of the invention is to provide a new technique for improving reception sensitivity in a piezoelectric element having a horizontal electrode structure.

A first aspect of the invention is directed to a piezoelectric element including a vibrating film, a piezoelectric body disposed on one surface side of the vibrating film, and a horizontal electrode structure in which electrodes are disposed at a predetermined gap therebetween on the piezoelectric body. The vibrating film includes a recess portion in a portion corresponding to the predetermined gap in plan view.

According to the first aspect of the invention, it is possible to improve the reception sensitivity of the piezoelectric element of the horizontal electrode structure. That is, by providing a recess portion in a portion of the vibrating film corresponding to the predetermined gap between the electrodes, distortion when receiving the elastic wave is concentrated on the recess portion, that is, the predetermined gap between the electrodes. Accordingly, since the inter-electrode portion of the piezoelectric body is mainly distorted, a potential difference (voltage) is increased and reception sensitivity is improved.

As a second aspect of the invention, the piezoelectric element according to the first aspect of the invention, which may also be configured such that a width of the recess portion along an electrode arrangement direction of the horizontal electrode structure is equal to or greater than the predetermined gap.

According to the second aspect of the invention, distortion can be concentrated on the entire predetermined gap between the electrodes by setting the width of the recess portion of the vibrating film to be equal to or greater than the predetermined gap between the electrodes.

According to a third aspect of the invention, the piezoelectric element according to the first or second aspect of the invention may be configured such that the predetermined gap is 2 μm or more and 8 μm or less.

As a fourth aspect of the invention, the piezoelectric element according to anyone of the first to third aspects of the invention may be configured such that, in the vibrating film, a boundary portion between the recess portion and a portion other than the recess portion is formed in a stepped shape, and a bottom surface of the recess portion is formed in a planar shape.

According to the fourth aspect of the invention, since the magnitude of distortion when receiving an elastic wave in a boundary portion between the recess portion of the vibrating film and a portion other than the recess portion is greatly changed, distortion can be more concentrated on the recess portion of the vibrating film.

As a fifth aspect of the invention, the piezoelectric element according to any one the first to fourth aspects of the invention may be configured such that the recess portion is a groove extending in a direction crossing an electrode arrangement direction of the horizontal electrode structure.

According to the fifth aspect of the invention, since the recess portion of the vibrating film is formed in a groove shape, a situation occurs in which relative distortion easily occurs between left and right portions between which the groove is interposed. That is, since distortion easily occurs in a direction crossing the groove direction, distortion when receiving the elastic wave is concentrated on the portion of the predetermined gap between the electrodes. Accordingly, since the inter-electrode portion of the piezoelectric body is mainly distorted, a further improvement in reception sensitivity can be expected.

As a sixth aspect of the invention, the piezoelectric element according to any one of the first to fifth aspects of the invention may be configured such that the piezoelectric body includes a recess portion in a portion of the predetermined gap.

According to the sixth aspect of the invention, also in a portion of the piezoelectric body corresponding to the gap between the electrodes, a recess portion is provided. Therefore, together with the recess portion of the vibrating film, stress when receiving the elastic wave can be more concentrated on the recess portion of the piezoelectric body that is a portion between the electrodes. As a result, a further improvement in reception sensitivity can be expected.

As a seventh aspect of the invention, the piezoelectric element according to the fifth aspect of the invention may be configured such that the piezoelectric body includes a groove-shaped recess portion, which is parallel to a groove direction of the recess portion of the vibrating film, in a portion of the predetermined gap.

According to the seventh aspect of the invention, also in a portion of the piezoelectric body corresponding to the gap between the electrodes, a groove-shaped recess portion parallel to the groove direction of the recess portion of the vibrating film is provided. Therefore, together with the recess portion of the vibrating film, stress when receiving the elastic wave can be more concentrated on the recess portion of the piezoelectric body that is a portion between the electrodes. As a result, a further improvement in reception sensitivity can be expected.

As an eighth aspect of the invention, the piezoelectric element according to any one of the first to seventh aspects of the invention may be configured such that side wall portions that are provided with the recess portion of the vibrating film interposed therebetween for supporting the vibrating film are further provided, and a width of the recess portion of the vibrating film may be 0.3 times or more and 0.8 times or less of a distance between the side wall portions.

According to the eighth aspect of the invention, it is possible to effectively improve the reception sensitivity by setting the width of the recess portion of the vibrating film to 0.3 times or more and 0.8 times or less of the distance between the side wall portions provided with the recess portion interposed therebetween.

As a ninth aspect of the invention, a piezoelectric element may be configured such that the piezoelectric element includes a vibrating film, a piezoelectric body disposed on one surface side of the vibrating film, and a horizontal electrode structure in which electrodes are disposed at a predetermined gap therebetween on the piezoelectric body, and in-plane distortion of the piezoelectric body is abruptly changed between a portion corresponding to the predetermined gap and a portion adjacent thereto in plan view, and in-plane distortion in the portion corresponding to the predetermined gap is larger than that in the portion adjacent to the portion corresponding to the predetermined gap.

According to the ninth aspect of the invention, since the in-plane distortion is concentrated on a portion of the piezoelectric body corresponding to a portion between the electrodes, a voltage generated between the electrodes is increased. As a result, it is possible to improve the reception sensitivity.

As a tenth aspect of the invention, a probe for receiving an ultrasonic wave may be configured to include the piezoelectric element according to any one of the first to ninth aspects of the invention.

According to the tenth aspect of the invention, since the ultrasonic wave is received by the piezoelectric element having the effect according to any one of the first to ninth aspects of the invention, it is possible to realize a probe that outputs the ultrasonic wave as an electrical signal. Therefore, it is possible to realize a probe with high reception sensitivity.

As an eleventh aspect of the invention, an ultrasonic measurement apparatus may be configured to include the probe according to the tenth aspect of the invention.

According to the eleventh aspect of the invention, it is possible to realize an ultrasonic measurement apparatus having the effect according to the tenth aspect of the invention. Therefore, it is possible to realize highly accurate measurement without increasing the irradiation intensity of the ultrasonic wave.

BRIEF DESCRIPTION OF THE DRAWINGS

The invention will be described with reference to the accompanying drawings, wherein like numbers reference like elements.

FIG. 6 is a diagram showing another configuration example of the piezoelectric element;

DESCRIPTION OF EXEMPLARY EMBODIMENTS (1) Ultrasonic Diagnostic Apparatus

Figure 1:
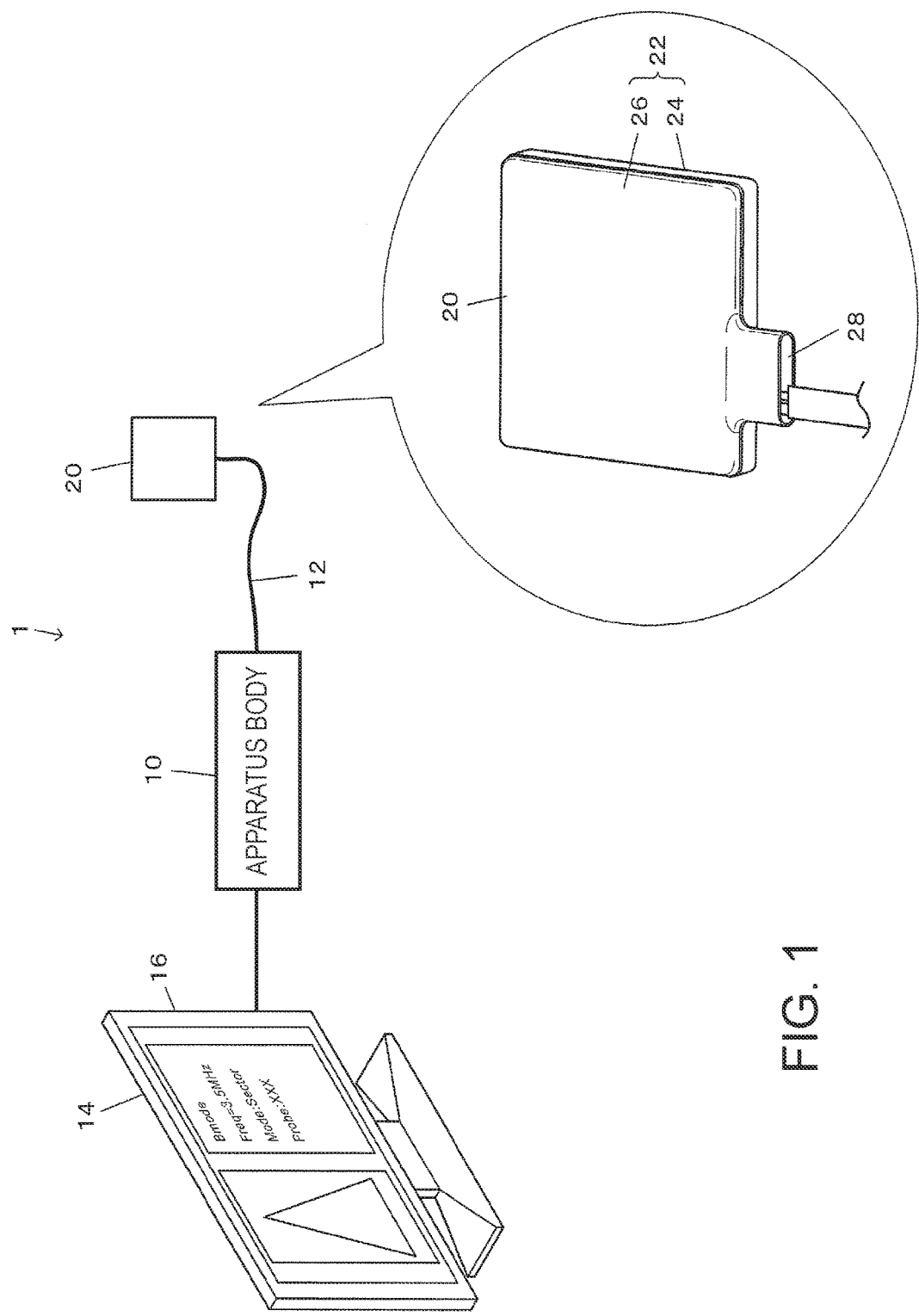
FIG. 1 is a diagram showing the schematic configuration of an ultrasonic measurement apparatus and the upper surface of an ultrasonic probe.

FIG. 1 is a diagram showing the schematic configuration of an ultrasonic measurement apparatus 1 and the upper surface of an ultrasonic probe 20 in the present embodiment. Referring to FIG. 1, the ultrasonic measurement apparatus 1 is an electronic apparatus that measures the biological information of a subject using an ultrasonic wave, and is configured to include an apparatus body 10 and the ultrasonic probe 20. The apparatus body 10 and the ultrasonic probe 20 are connected to each other by a cable 12, so that a drive signal is transmitted to the ultrasonic probe 20 from the apparatus body 10 and a detection signal is transmitted to the apparatus body 10 from the ultrasonic probe 20.

In addition, a display device 14 is connected to the apparatus body 10. The display device 14 includes a display panel 16, and displays, for example, an image based on a detection signal from the ultrasonic probe 20 on the display panel 16 according to a display signal from the apparatus body 10. The display device 14 is provided separately from the apparatus body 10. However, a structure may be adopted in which the display device 14 and the apparatus body 10 are integrally formed.

(2) Ultrasonic Probe

In the ultrasonic probe 20, a thin rectangular parallelepiped housing 22 is formed by bonding a front side body 26 and a back side body 24 to each other, and an ultrasonic device unit 40 (shown in FIG. 3) is provided inside the housing 22. The cable 12 is connected to the ultrasonic device unit 40 in the housing 22 through a cable port 28 formed between the bonding surfaces of the front side body 26 and the back side body 24. The ultrasonic device unit 40 transmits an ultrasonic wave according to a drive signal from the apparatus body 10, receives a reflected wave of the ultrasonic wave, and outputs a signal of the received reflected wave to the apparatus body 10 as a detection signal.

Figure 2:
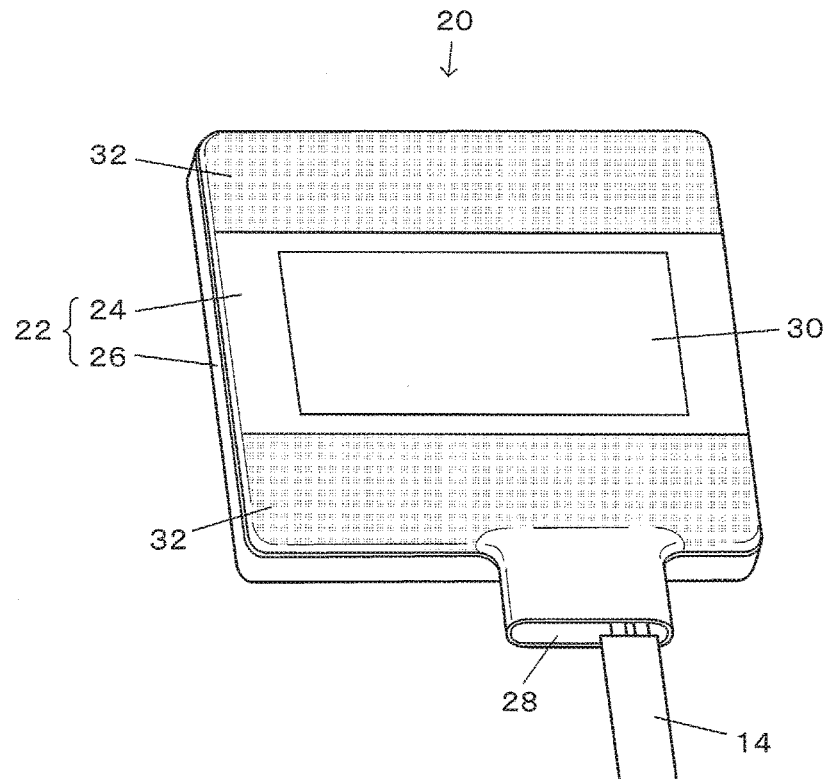
FIG. 2 is a diagram showing the lower surface of an ultrasonic probe.

FIG. 2 is a bottom view of the ultrasonic probe 20. An acoustic matching portion 30 is provided in the central portion of the back side body 24, and a contact portion 32 is provided on the upper and lower sides of the acoustic matching portion 30. The outer surface of the acoustic matching portion 30 and the outer surface of the contact portion 32 are formed so as to be even with each other or formed so that the outer surface of the acoustic matching portion 30 protrudes from the outer surface of the contact section. The acoustic matching portion 30 and the contact portion 32 are brought into contact with the skin surface of the measurement target part of the subject, so that the ultrasonic probe 20 is attached to the skin surface. The ultrasonic device unit 40 is provided so as to be located immediately below the acoustic matching portion 30 in the housing 22. The acoustic matching portion 30 is formed of a material having an acoustic impedance (for example, 1.0 [MRayl] to 1.5 [MRayl]) close to the acoustic impedance 1.5 [MRayl] of the body. For example, the acoustic matching portion 30 is formed of silicon resin. The contact portion 32 is formed of an adhesive material that is detachable from the skin surface of the measurement target part, for example.

(3) Ultrasonic Device Unit

Figure 3:
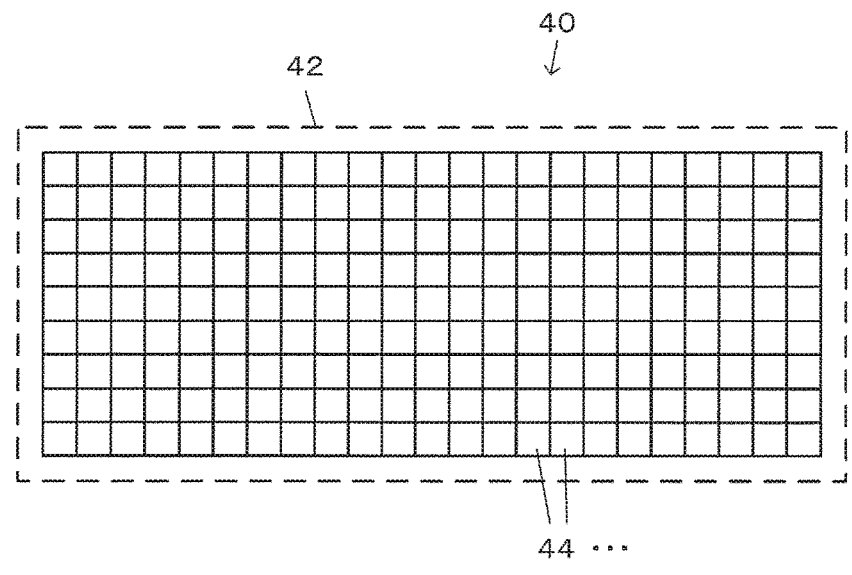
FIG. 3 is a conceptual diagram of an ultrasonic device unit.

FIG. 3 is a diagram conceptually showing the configuration of the ultrasonic device unit 40. The ultrasonic device unit 40 is disposed immediately below the acoustic matching portion 30 when viewed from the back surface side of the housing 22 (in FIG. 2), and is configured to include an element array 42 in which a plurality of ultrasonic transducers 44 are disposed in a two-dimensional array. That is, in the element array 42, the ultrasonic transducers 44 of N rows are arranged in a first direction FR (slice direction), and the ultrasonic transducers 44 of L columns are arranged in a second direction SR (scanning direction) perpendicular to the first direction FR. One ultrasonic transducer 44 is configured as a transducer element chip including a transmission element, which transmits an ultrasonic wave, and a receiving element, which is a piezoelectric element that receives a reflected wave of the ultrasonic wave. Since the present embodiment is related with the characteristics of the receiving element of the ultrasonic transducer 44, the receiving element will be described in more detail below.

(4) Piezoelectric Element as a Receiving Element

Figure 4:
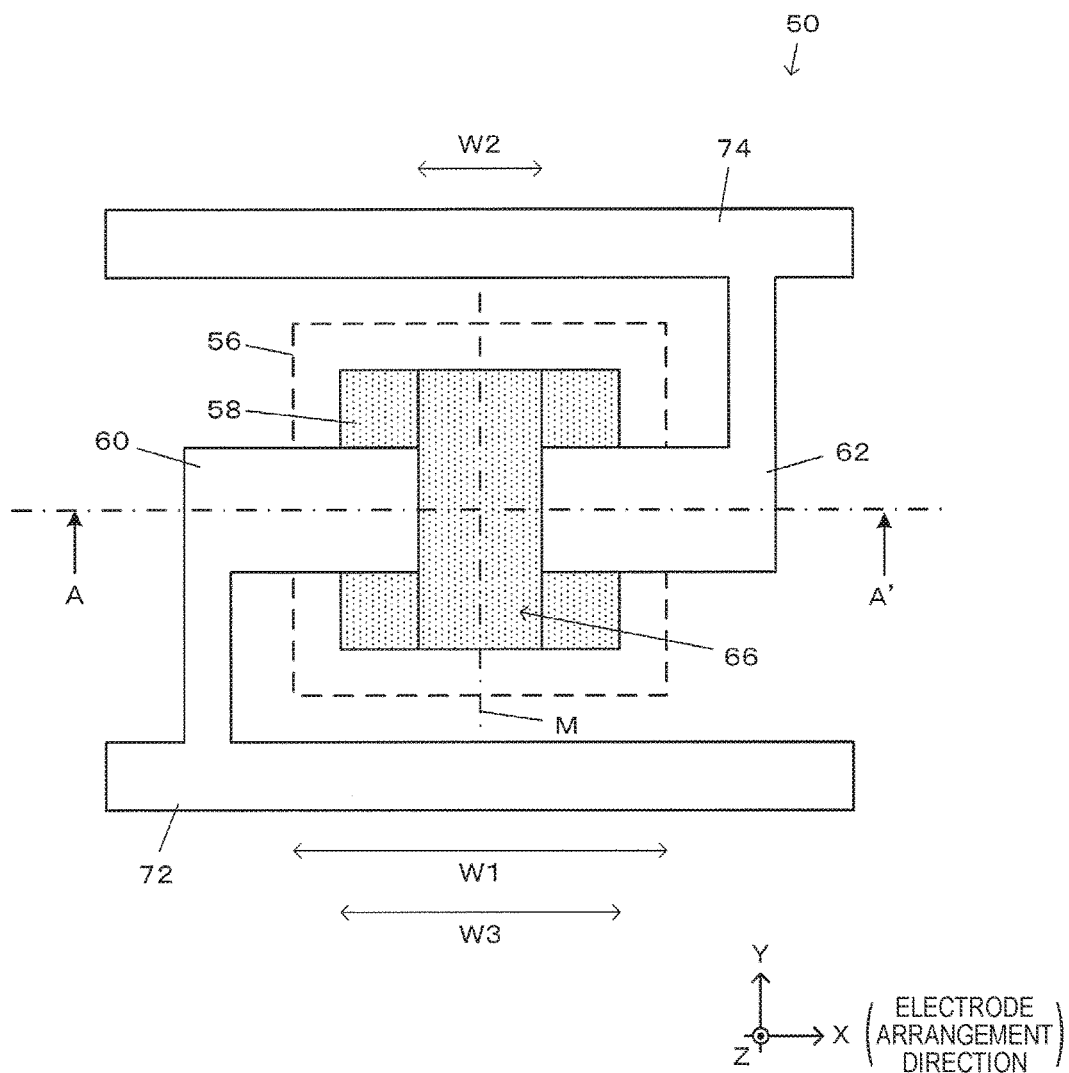
FIG. 4 is a plan view of a piezoelectric element (receiving element)
Figure 5:
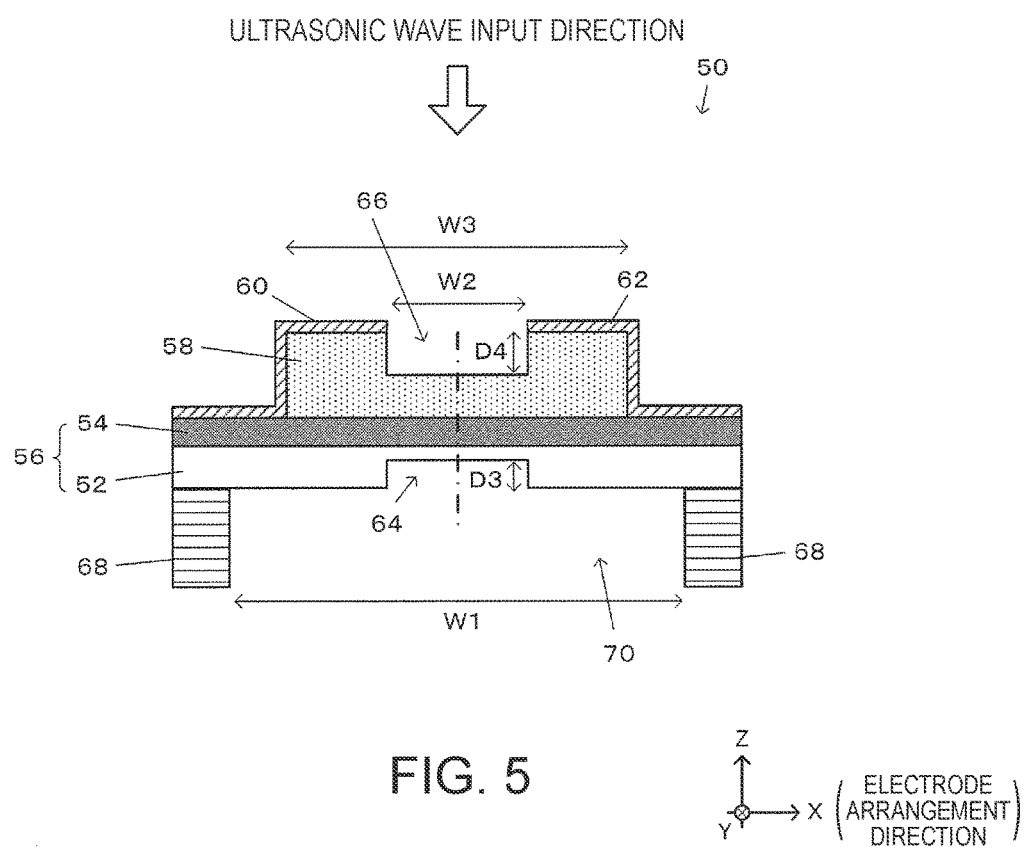
FIG. 5 is a sectional view of a piezoelectric element.

The receiving element is formed by a piezoelectric element 50. FIG. 4 is a plan view of the piezoelectric element 50, and FIG. 5 is a sectional view taken along the line A-A' of FIG. 4. Referring to FIGS. 4 and 5, the piezoelectric element 50 is configured to include a vibrating film 56, a piezoelectric body 58 disposed on one surface side of the vibrating film 56, and first and second electrodes 60 and 62 that form horizontal electrode structure disposed on the upper surface (surface not facing the vibrating film 56) of the piezoelectric body 58.

The vibrating film 56 is formed as a flexible film by laminating a silicon oxide ($SiO_2$) layer 52 and a zirconium oxide ($ZrO_2$) layer 54. A thickness between 200 nm to 1500 nm can be adopted as atypical thickness of the silicon oxide layer 52, and 200 nm to 1500 nm can be adopted as a typical thickness of the zirconium oxide layer 54.

The piezoelectric body 58 is formed of, for example, lead zirconate titanate (PZT). A thickness between 200 nm to 2000 nm can be adopted as a typical thickness of the piezoelectric body 58. If the thickness of the piezoelectric body 58 is smaller than 200 nm, the amount of lead (Pb) that escapes to the lower layer is increased when baking the piezoelectric body. If the thickness of the piezoelectric body 58 is larger than 2000 nm, the vibrating film 56 is difficult to bend. In any case, the reception sensitivity is lowered.

The first and second electrodes 60 and 62 are formed of a conductive material, such as iridium (Ir), and have a horizontal electrode structure in which the first and second electrodes 60 and 62 are disposed on the upper surface of the piezoelectric body 58 with a predetermined gap W2 therebetween. The gap W2 between the first and second electrodes 60 and 62 is 2 μm or more and 8 μm or less. The first electrode 60 is connected to a first electrode line 72, and the second electrode 62 is connected to a second electrode line 74.

Both of the vibrating film 56 and the piezoelectric body 58 have rectangular shapes in plan view, and are formed so that the respective sides are parallel and the centers match each other. In addition, the first and second electrodes 60 and 62 are disposed so as to be line-symmetric with respect to the centerline M parallel to one side of the piezoelectric body 58.

On the other surface side (surface not facing the piezoelectric body 58) of the vibrating film 56, in order to support the piezoelectric element 50 and form a cavity (opening) 70 for receiving an ultrasonic wave that is an elastic wave, silicon side walls 68 that are side wall portions are disposed so as to interpose a first recess portion 64 of the vibrating film 56.

The piezoelectric element 50 is used so that the ultrasonic wave is input from a side opposite to the cavity 70, that is, the upper side in FIG. 5. The resonance frequency of the vibrating film 56 in the electrode arrangement direction corresponds to an ultrasonic frequency $f_0$ to be received. For example, in a case where the ultrasonic frequency $f_0$ is 2 MHz to 20 MHz, it is preferable that a gap W1 between the silicon side walls 68 is 15 μm to 60 μm. In the piezoelectric element 50, the vibrating film 56 is disposed toward the back surface side of the housing 22, so that the vibrating film 56 vibrates in response to an elastic wave (in the present embodiment, an ultrasonic wave) received through the acoustic matching portion 30.

(5) Recess Portion

As a feature of the present embodiment, in the piezoelectric element 50, the first recess portion 64 is formed on the other surface side (side opposite to the piezoelectric body 58 side) of the vibrating film 56 so as to overlap a gap portion between the first and second electrodes 60 and 62 of the piezoelectric body 58 in plan view, and a second recess portion 66 is formed in a gap portion between the first and second electrodes 60 and 62 of the piezoelectric body 58. The first and second recess portions 64 and 66 are provided at corresponding positions on the front and back surfaces of the piezoelectric element 50. An improvement in the reception sensitivity of the piezoelectric element 50 is realized by the first and second recess portions 64 and 66.

In FIGS. 4 and 5, both of the first and second recess portions 64 and 66 are formed in a groove shape extending in a direction (Y-axis direction) crossing the electrode arrangement direction (X-axis direction) of the horizontal electrode structure, and are line-symmetric with respect to the centerline M of the piezoelectric body 58 in plan view (when viewed from the positive direction to the negative direction of the Z axis). Specifically, each of the first and second recess portions 64 and 66 forms a groove having a rectangular parallelepiped shape in which a boundary portion between a recess portion and a portion other than the recess portion is stepped and the bottom surface of the recess portion is formed in a planar shape. In the present embodiment, the length of the first recess portion 64 in the lateral direction (X-axis direction) is equal to the gap W2 between the first and second electrodes 60 and 62, and the length of the first recess portion 64 in the groove direction (Y-axis direction) is larger than the gap W2 and is equal to the length of the vibrating film 56 in the longitudinal direction in FIG. 4. In addition, the depth D3 of the first recess portion 64 is less than the thickness of the vibrating film 56.

In the present embodiment, the length of the second recess portion 66 in the lateral direction (X-axis direction) is equal to the gap W2 between the first and second electrodes 60 and 62 (that is, equal to the length of the first recess portion 64 in the lateral direction), and the length of the second recess portion 66 in the groove direction (Y-axis direction) is larger than the gap W2 and is equal to the length of the piezoelectric body 58 in the longitudinal direction in FIG. 4. In addition, the depth D4 of the second recess portion 66 is less than the thickness of the piezoelectric body 58.

FIG. 5 shows a case where the depth D3 of the first recess portion 64 is less than the thickness of the silicon oxide layer 52 that forms the lower layer of the vibrating film 56. However, as shown in FIG. 6, a case can also be considered in which the depth D3 of the first recess portion 64 is larger than the thickness of the silicon oxide layer 52 so as to reach the zirconium oxide layer 54.

(6) Reception Processing

In the ultrasonic wave receiving processing of the piezoelectric element 50, a signal (that is, an electrical signal) of a potential difference corresponding to the received ultrasonic wave appears between the first electrode line 72 (also referred to as the first electrode 60) and the second electrode line 74 (also referred to as the second electrode 62), and is output as a detection signal. More specifically, an ultrasonic wave transmitted from the transmission element of the ultrasonic transducer 44 is reflected in the body of a subject, and the vibrating film 56 receives the reflected wave (elastic wave) to vibrate itself. Since the vibrating film 56 and the piezoelectric body 58 are integrally formed, the piezoelectric body 58 is distorted if the vibrating film 56 is deformed by ultrasonic vibration. Surface charges corresponding to the distortion are generated in the piezoelectric body 58, a potential difference (voltage) is generated between the first and second electrodes 60 and 62, and the generated potential difference (voltage) is taken out as a detection signal due to the piezoelectric effect occurring between the first and second electrodes 60 and 62. Since the detection signal of the piezoelectric element 50 is detected in units of the ultrasonic transducer 44, a detection signal is obtained in units of a dot matrix as shown in FIG. 3.

(7) Reception Sensitivity Due to Recess Portions

Next, an improvement in the reception sensitivity due to providing a recess portion in the piezoelectric element will be described.

(7a) Presence or Absence of a Groove and the Depth of a Groove

Figure 7A:
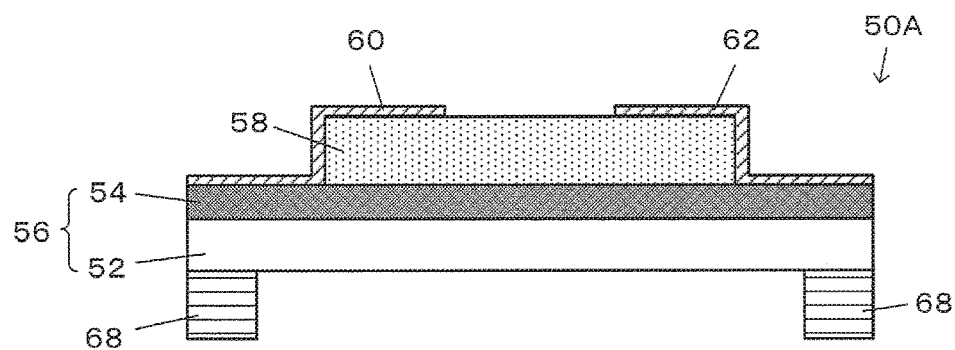
FIGS. 7A to 7C are diagrams showing the configurations of receiving elements in which the presence or absence of a recess portion is different.
Figure 7B:
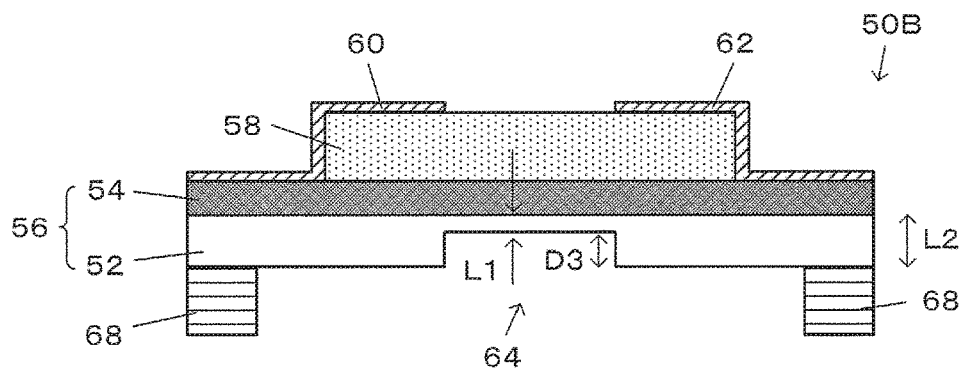
Figure 7C:
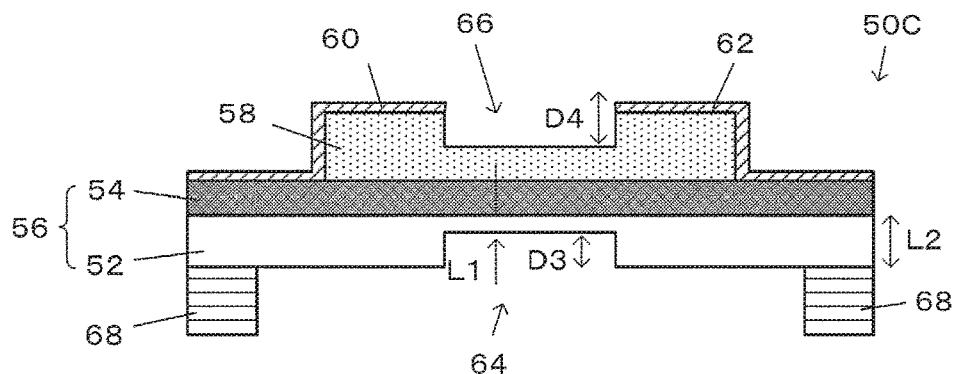

FIGS. 7A to 7C and 8 are diagrams for explaining a difference in reception sensitivity due to the presence or absence of a recess portion in the piezoelectric element 50. FIGS. 7A to 7C are sectional views showing the structures of three kinds of piezoelectric elements 50A to 50C to be compared with each other. The structures of the piezoelectric elements 50A to 50C are different in terms of the presence or absence of a recess portion. That is, no recess portion is formed in a piezoelectric element 50A as shown in FIG. 7A, only the first recess portion 64 is formed in a piezoelectric element 50B as shown in FIG. 7B, and the first and second recess portions 64 and 66 are formed in a piezoelectric element 50C as shown in FIG. 7C. In both of the first and second recess portions 64 and 66, the width of the recess portion is the same as the gap W2 between electrodes of the horizontal electrode structure, and the piezoelectric element 50C corresponds to the piezoelectric element 50 (refer to FIGS. 4 and 5) of the present embodiment.

Figure 8:
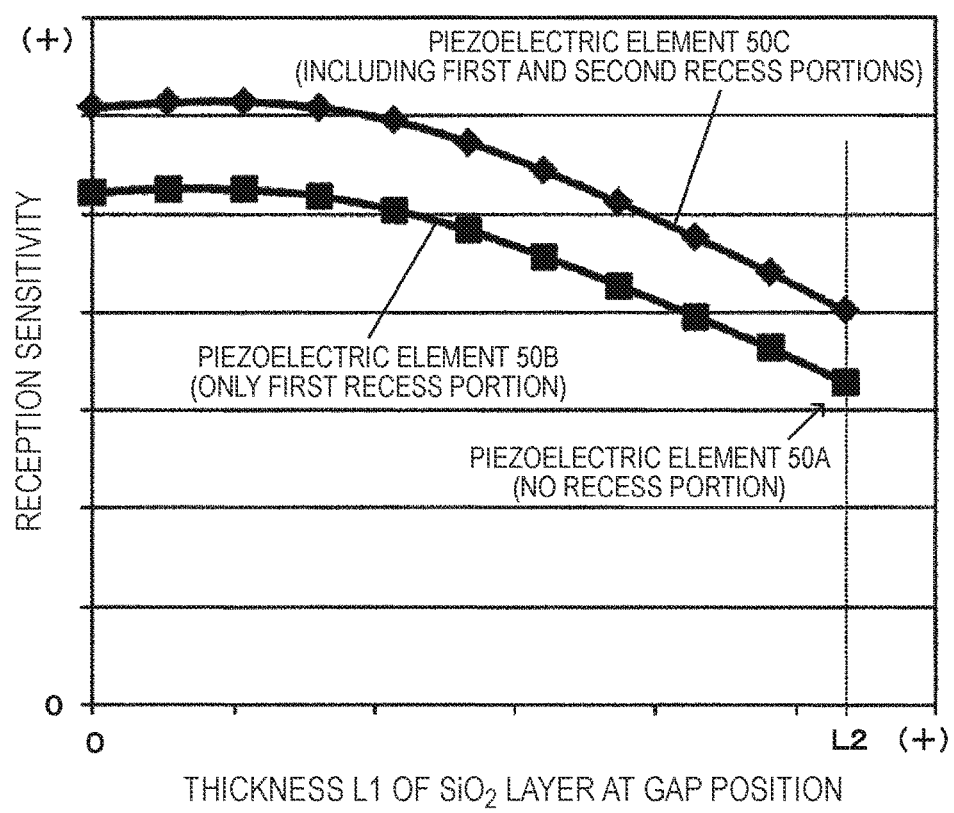
FIG. 8 is a graph showing a difference in reception sensitivity due to the presence or absence of a recess portion.

FIG. 8 is a graph showing the reception sensitivity calculated by simulation for the three piezoelectric elements 50A to 50C shown in FIGS. 7A to 7C. In this graph, the horizontal axis indicates the thickness L1 (that is, a value obtained by subtracting the depth D3 of the first recess portion 64 from the thickness L2 of the silicon oxide layer 52) of the silicon oxide layer 52 corresponding to a gap (electrode gap portion of the horizontal electrode structure), and the vertical axis indicates reception sensitivity. The gap W1 between the silicon side walls 68 is adjusted so that the natural frequency of the piezoelectric element 50 is 8.6 MHz at any point on the graph.

For the piezoelectric elements 50B and 50C, reception sensitivity in the case of changing the thickness L1 of the silicon oxide layer 52 corresponding to the gap (electrode gap portion of the horizontal electrode structure) in a range of "0" to the thickness L2 of the silicon oxide layer 52 was calculated. That is, reception sensitivity in the case of changing the depth D3 of the first recess portion 64 was calculated. However, for the piezoelectric element 50C, the depth D4 of the second recess portion 66 was fixed to the half of the thickness of the piezoelectric body 58. A case where the depth D3 of the first recess portion 64 is set to "0" (D3=0) (that is, the thickness L1 of the silicon oxide layer 52 corresponding to the gap is set to the thickness L2 (L1=L2) of the silicon oxide layer 52) for the piezoelectric element 50B corresponds to the reception sensitivity in the piezoelectric element 50A.

According to the graph shown in FIG. 8, it can be seen that the reception sensitivity increases as the thickness L1 of the silicon oxide layer 52 corresponding to the gap decreases (that is, as the depth D3 of the first recess portion 64 increases) for both of the piezoelectric elements 50B and 50C. In addition, for any thickness L1, reception sensitivity in the piezoelectric element 50C is better than that in the piezoelectric element 50B. However, the manner of change in the reception sensitivity with respect to the thickness L1 is not uniform. In a range in which the thickness L1 is relatively large (in FIG. 8, a thickness of about ⅓ or more of the thickness L2), the reception sensitivity increases uniformly as the thickness L1 decreases. However, in a range in which the thickness L1 is relatively small (in FIG. 8, a thickness of about ⅓ or less of the thickness L2), the reception sensitivity is almost constant.

(7b) In-Plane Distortion

Figure 9A:
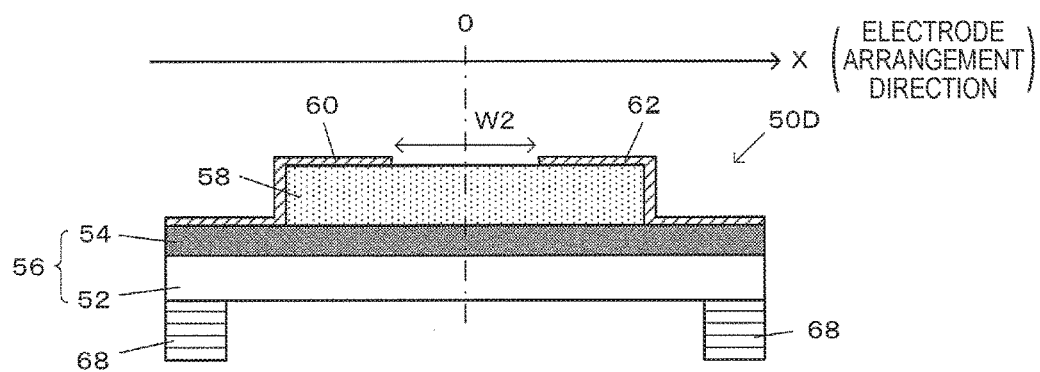
FIGS. 9A and 9B are diagrams showing the configurations of receiving elements which differ in the presence or absence of a recess portion.
Figure 9B:
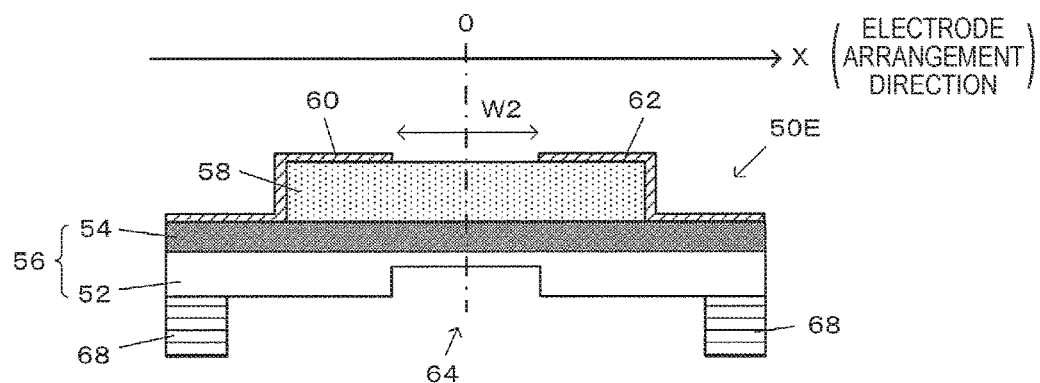
Figure 10:
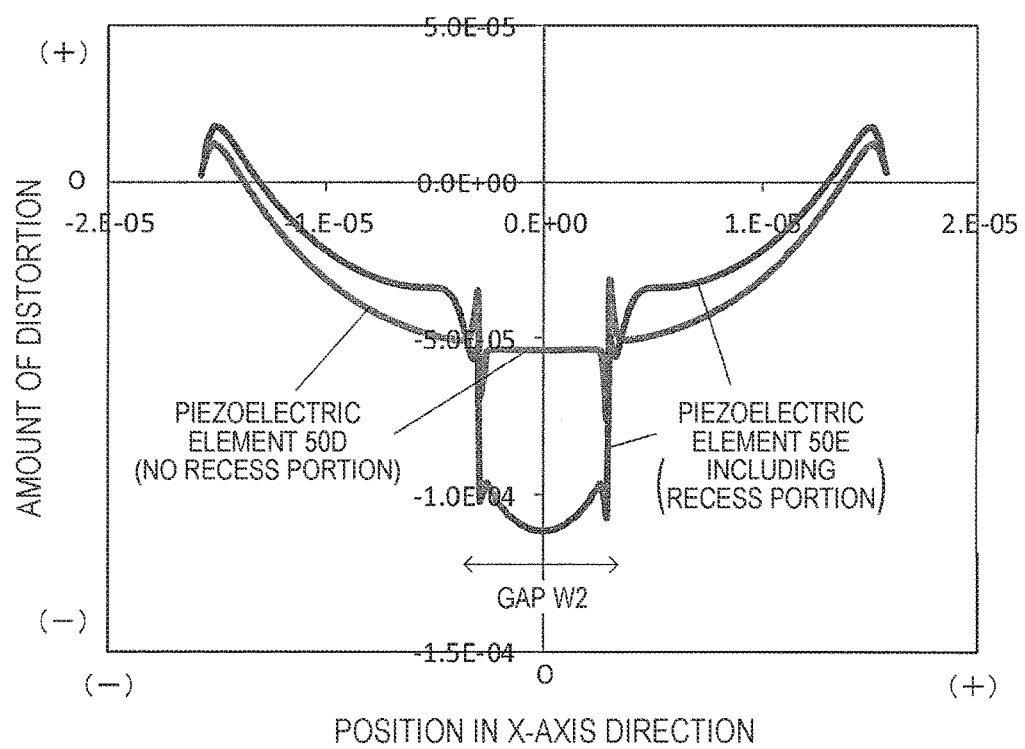
FIG. 10 is a graph showing a difference in in-plane distortion due to the presence or absence of a recess portion.

FIGS. 9A, 9B, and 10 are diagrams for explaining a difference in "in-plane distortion" occurring in the piezoelectric body 58 due to the presence or absence of a recess portion in the piezoelectric element 50. FIGS. 9A and 9B are sectional views showing the structures of two kinds of piezoelectric elements 50D and 50E to be compared with each other. The structures of the piezoelectric elements 50D and 50E are different in terms of the presence or absence of the first recess portion 64. That is, in the piezoelectric element 50D, no recess portion is formed as shown in FIG. 9A. However, in the piezoelectric element 50E, the first recess portion 64 is formed as shown in FIG. 9B. In addition, the width of the first recess portion 64 is the same as the gap W2 between the electrodes of the horizontal electrode structure, and the second recess portion 66 is not formed in each of the piezoelectric elements 50D and 50E.

FIG. 10 is a graph showing in-plane distortion occurring in the piezoelectric body 58 that has been calculated by simulation for the two piezoelectric elements 50D and 50E shown in FIGS. 9A and 9B. At this time, a pressure of 1 atmosphere is applied to the piezoelectric body 58 from above. In this graph, the horizontal axis indicates a position along the electrode arrangement direction (X-axis direction), and the vertical axis indicates the amount of distortion in the electrode arrangement direction (X-axis direction) occurring on the upper surface of the piezoelectric body 58. In the horizontal axis, the center position of the piezoelectric body 58 in the left and right direction (center of the horizontal electrode structure in the electrode arrangement direction: center in a direction perpendicular to the groove direction of the first recess portion 64) in FIGS. 9A and 9B is set to "0".

According to the graph shown in FIG. 10, both of the piezoelectric elements 50D and 50E are distorted such that the amount of distortion increases toward the center of the piezoelectric body 58. Specifically, for the piezoelectric element 50D, the amount of distortion changes smoothly toward the central portion from the end of the piezoelectric body 58. On the other hand, for the piezoelectric element 50E, the amount of distortion is abruptly changed at a boundary position between a portion corresponding to the first recess portion 64 and a portion adjacent thereto, and the amount of distortion in the portion corresponding to the first recess portion 64 is very large compared with that in the other portions. When the piezoelectric elements 50D and 50E are compared to each other, for a portion corresponding to the first recess portion 64, the amount of distortion of the piezoelectric element 50E is very large compared with that of the piezoelectric element 50D. However, in a portion other than the portion corresponding to the first recess portion 64, the amount of distortion of the piezoelectric element 50D is larger than that of the piezoelectric element 50E.

That is, it can be seen that in-plane distortion is concentrated on the position of the piezoelectric body 58 corresponding to the first recess portion 64 by providing the first recess portion 64 in the vibrating film 56 of the piezoelectric element 50. Therefore, by providing the first recess portion 64 in a portion of the vibrating film 56 corresponding to the gap (electrode gap portion of the horizontal electrode structure), it is possible to concentrate the distortion on the gap portion of the piezoelectric body 58 (electrode gap portion of the horizontal electrode structure). As a result, since a voltage generated between the first and second electrodes 60 and 62 increases, reception sensitivity is improved.

(7c) In-Plane Distortion

Figure 11A:
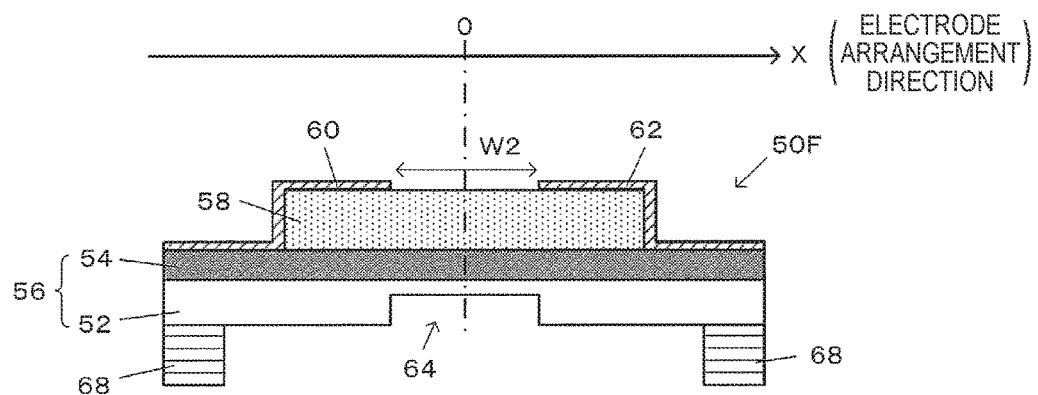
FIGS. 11A and 11B are diagrams showing the configuration of a piezoelectric element.
Figure 11B:
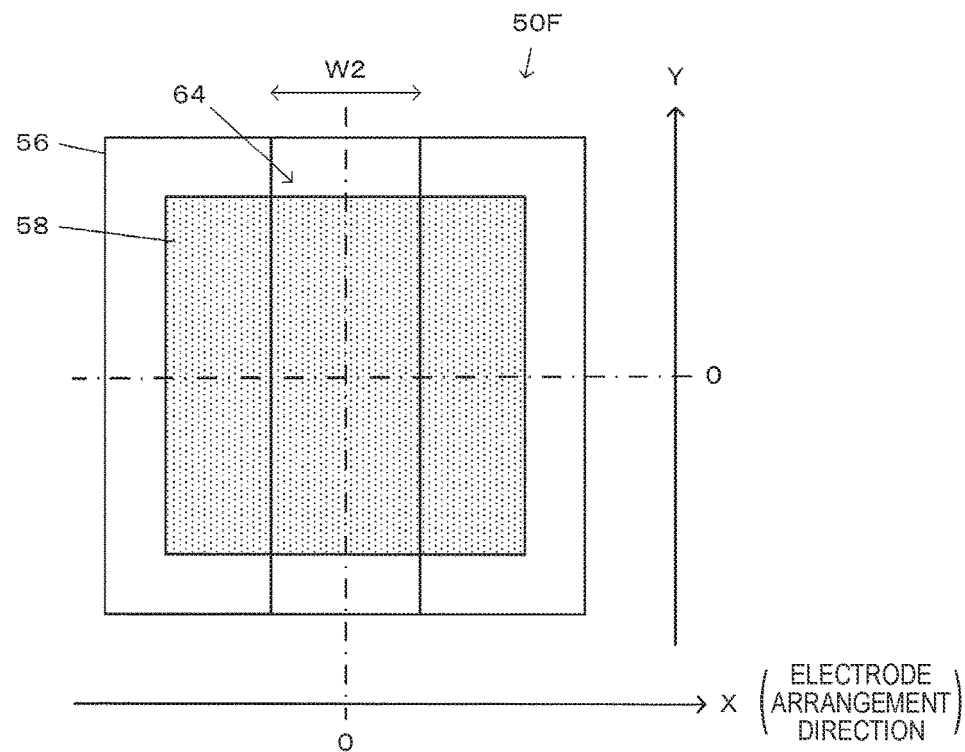
Figure 12:
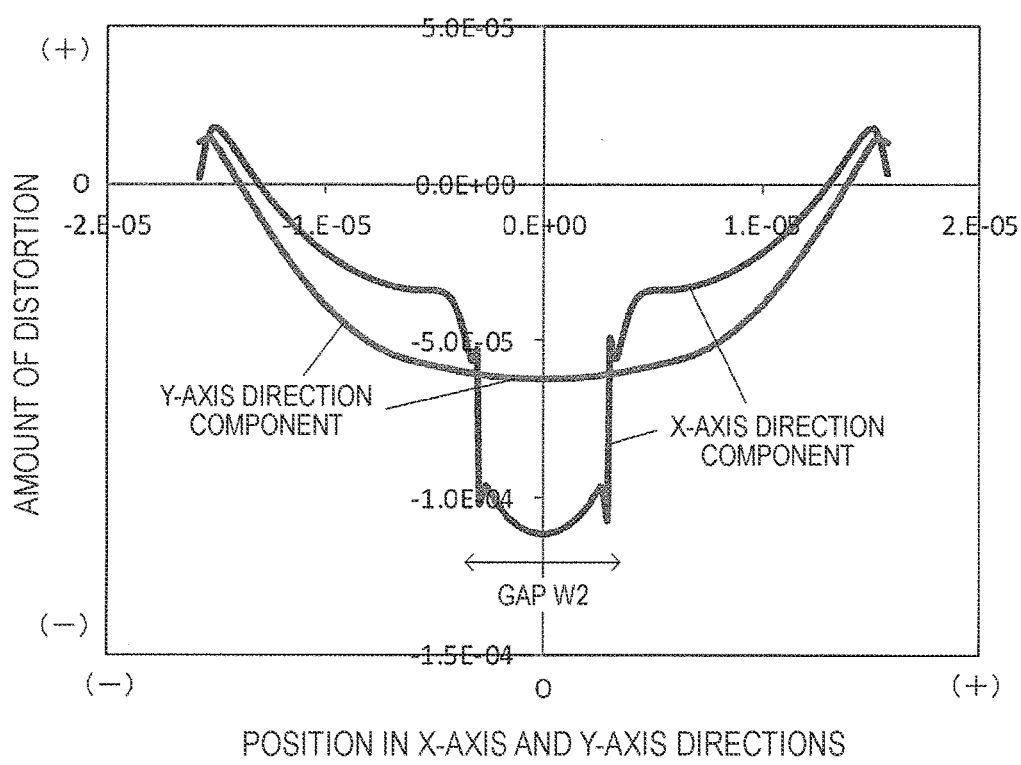
FIG. 12 is a graph of each direction component of in-plane distortion.

FIGS. 11P, 11B, and 12 are diagrams for explaining a difference in a direction component of "in-plane distortion" occurring in the piezoelectric body 58 of the piezoelectric element 50. FIGS. 11A and 11B are diagrams showing the structure of a piezoelectric element 50F. FIG. 11A is a sectional view of the piezoelectric element 50F, and FIG. 11B is a plan view showing the arrangement relationship between the piezoelectric body 58 of the piezoelectric element 50F and the vibrating film 56. The piezoelectric element 50F includes the first recess portion 64 having the same width as the gap W2 between the electrodes of the horizontal electrode structure, and the second recess portion 66 is not provided.

FIG. 12 is a graph showing two-direction components of in-plane distortion occurring in the piezoelectric body 58 that have been calculated by simulation for the piezoelectric element 50F shown in FIGS. 11A and 11B. Two directions are an electrode arrangement direction (X-axis direction) shown in FIG. 11B and a longitudinal direction (Y-axis direction) of the first recess portion 64 perpendicular to the electrode arrangement direction (X-axis direction). In the graph shown in FIG. 12, the horizontal axis indicates a position along each of the X-axis direction and the Y-axis direction in a case where the center position of the gap of the horizontal electrode structure is set to 0, and the vertical axis indicates the amount of distortion of the piezoelectric body 58 in each of the X-axis direction and the Y-axis direction. Therefore, in the graph shown in FIG. 12, a component in the Y-axis direction indicates the amount of distortion at a position in the Y-axis direction in the gap of the horizontal electrode structure, and a component in the X-axis direction indicates the amount of distortion in the electrode arrangement direction (X-axis direction) including the gap of the horizontal electrode structure. The amount of distortion in the X-axis direction corresponds to the amount of distortion in the X-axis direction (electrode arrangement direction) for the piezoelectric element 50E shown in FIG. 10.

According to the graph shown in FIG. 12, the magnitude of both the X-axis direction component and the Y-axis direction component of the in-plane distortion increases toward the central portion (central portion of the gap of the horizontal electrode structure) from the end of the piezoelectric body 58. Specifically, the Y-axis direction component of the in-plane distortion changes gradually toward the central portion from the end of the piezoelectric body 58. On the other hand, the X-axis direction component of the in-plane distortion abruptly changes at a boundary position between a portion corresponding to the first recess portion 64 and the other portions, and the amount of distortion in the portion corresponding to the first recess portion 64 is very large compared with that in the other portions. Focusing on the portion (portion including the center of the piezoelectric body 58) corresponding to the gap, the magnitude of the X-axis direction component of the amount of distortion is about twice the magnitude of the Y-axis direction component.

Therefore, it is possible to effectively improve the reception sensitivity of the piezoelectric element by arranging electrodes so as to face each other in a direction crossing the longitudinal direction (groove direction: Y-axis direction) of the first recess portion 64 with the first recess portion 64 interposed therebetween.

Effects

Thus, according to the present embodiment, it is possible to improve the reception sensitivity by forming a groove-shaped recess portion in each of the vibrating film 56 and the piezoelectric body 58 corresponding to a gap between electrodes in the piezoelectric element 50 of the horizontal electrode structure. That is, the first recess portion 64 is formed in a portion of the vibrating film 56, which is a gap position of the horizontal electrode structure in plan view, so that the groove direction crosses the electrode arrangement direction. Similarly, the second recess portion 66 is formed in a portion of the piezoelectric body 58 so that the groove direction crosses the electrode arrangement direction. Accordingly, since distortion occurring in the vibrating film 56 due to ultrasonic waves is eventually concentrated on the second recess portion 66 of the piezoelectric body 58, a potential difference (voltage) between electrodes is increased. As a result, reception sensitivity is improved.

Since recess portions (first and second recess portions 64 and 66) are provided in portions corresponding to the gap between electrodes in plan view in both of the vibrating film 56 and the piezoelectric body 58, stress when receiving the ultrasonic wave, which is an elastic wave, is easily concentrated on the first and second recess portions 64 and 66 in the entire piezoelectric element 50. Accordingly, reception sensitivity is improved.

In addition, by configuring the ultrasonic probe 20 including the piezoelectric element 50 of the present embodiment or configuring the ultrasonic measurement apparatus 1 including the ultrasonic probe 20, it is possible to realize a probe and an ultrasonic measurement apparatus capable of performing highly accurate ultrasonic measurement without increasing the irradiation intensity of the ultrasonic wave.

Modification Examples

In addition, it should be understood that embodiments to which the invention can be applied are not limited to the embodiment described above and various modifications can be made without departing from the spirit and scope of the invention.

(A) Width of a Recess Portion

Figure 13:
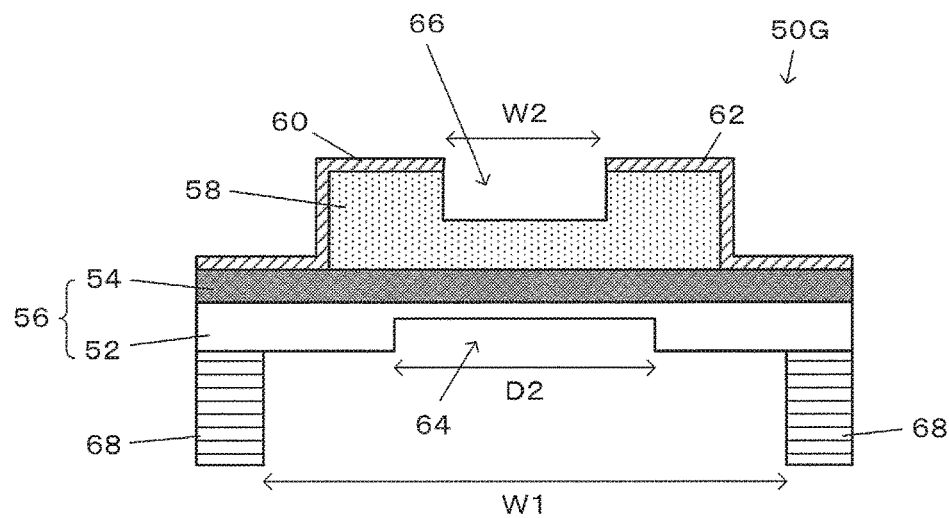
FIG. 13 is a diagram showing another configuration example of the piezoelectric element.

In the embodiment described above, the width of the first recess portion 64 and the width of the second recess portion 66 are equally set to the gap W2 between the first and second electrodes 60 and 62. However, as shown in FIG. 13, the width D2 of the first recess portion 64 may be set to be larger (longer) than the gap W2 between the electrodes.

Figure 14:
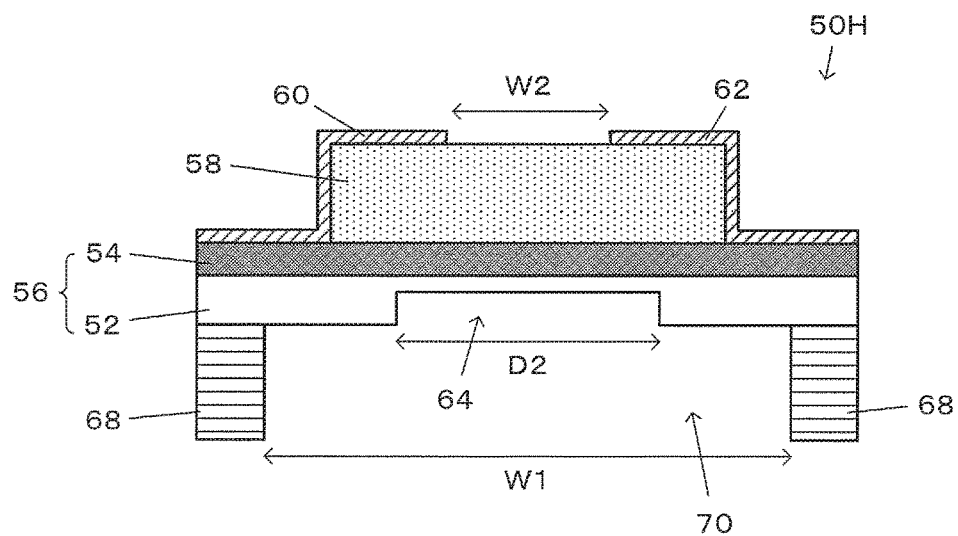
FIG. 14 is a diagram showing the configuration of a piezoelectric element in which the width of a first recess portion is differs from the previous embodiments.
Figure 15:
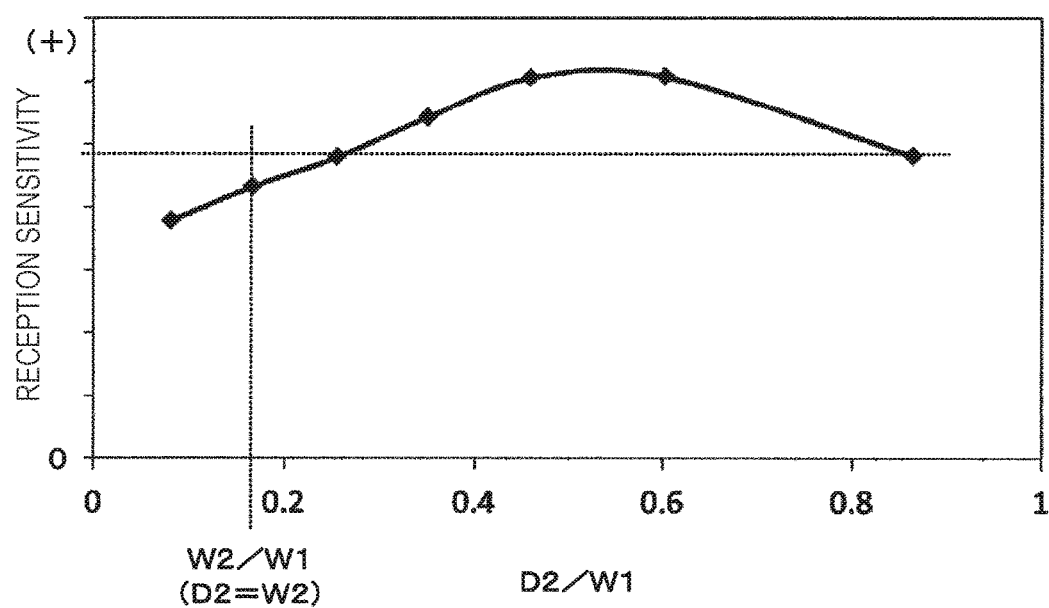
FIG. 15 is a graph showing a difference in reception sensitivity due to the width of the first recess portion.

In this case, a difference in the reception sensitivity of the piezoelectric element 50 occurs due to the width D2 of the first recess portion 64. FIGS. 14 and 15 are diagrams for explaining a difference in reception sensitivity due to the difference in the width D2 of the first recess portion 64 in the piezoelectric element 50. FIG. 14 is a diagram showing the structure of a piezoelectric element 50H. In the piezoelectric element 50H, the first recess portion 64 is formed, and the second recess portion 66 is not formed.

FIG. 15 is a graph showing a change in reception sensitivity with respect to the width D2 of the first recess portion 64 that has been calculated by simulation for the piezoelectric element 50H. In this graph, the horizontal axis indicates a ratio D2/W1 of the width D2 of the first recess portion 64 to the gap W1 between the silicon side walls 68, and the vertical axis indicates reception sensitivity. Reception sensitivity in the case of changing the width D2 of the first recess portion 64 in a range in which the ratio D2/W1 is 0.1 to 0.9. The gap W1 between the silicon side walls 68 is adjusted so that the natural frequency of the piezoelectric element 50 is 8.6 MHz at any point on the graph.

The ratio D2/W1 in a case where the width D2 of the first recess portion 64 is the same as the gap W2 between electrodes is about 0.16. Therefore, it can be seen from the graph shown in FIG. 15 that reception sensitivity is improved by setting the width D2 of the first recess portion 64 to be larger than the gap W2 between electrodes. When the ratio D2/W1 is about 0.5, that is, when the width D2 of the first recess portion 64 is about ½ of the gap W1 between the silicon side walls 68, reception sensitivity is maximized. It can be said that setting the ratio D2/W1 of the width D2 of the first recess portion 64 to the gap W1 between the silicon side walls 68 to 0.3 or more and 0.8 or less is suitable for the improvement in reception sensitivity.

(B) First Recess Portion 64 Only

Figure 16:
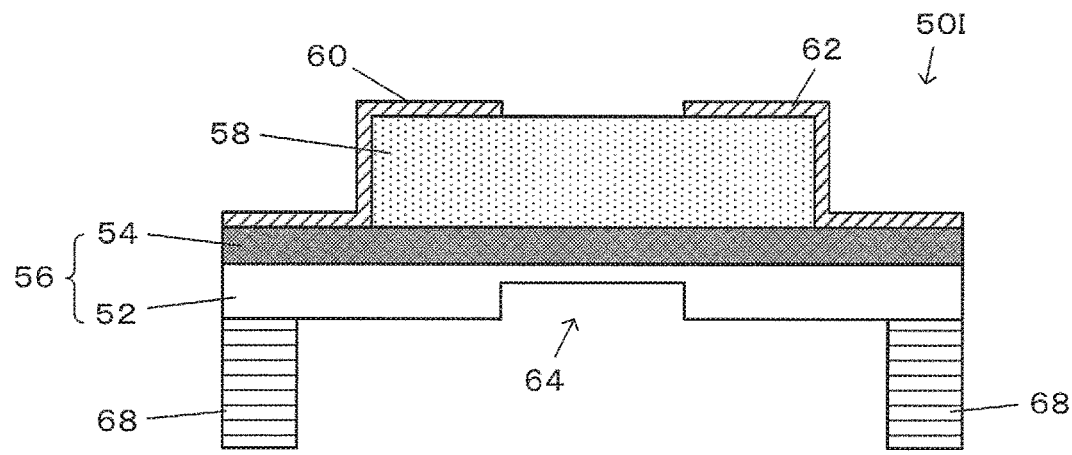
FIG. 16 is a diagram showing another configuration example of the piezoelectric element.

The second recess portion 66 may not be provided as in a piezoelectric element 50I shown in FIG. 16. As described above with reference to FIGS. 9A, 9B, and 10, since the first recess portion 64 is present, distortion of the piezoelectric body 58 in the in-plane direction when receiving the ultrasonic wave that is an elastic wave is concentrated on the first recess portion 64, that is, on the gap portion between the electrodes. Therefore, even if a piezoelectric element is configured such that only the first recess portion 64 on the vibrating film 56 side is provided and no recess portion is provided in the piezoelectric body 58, a significant improvement in reception sensitivity can be expected compared with a configuration in which even the first recess portion 64 is not provided.

(C) Projection Portion

Figure 17:
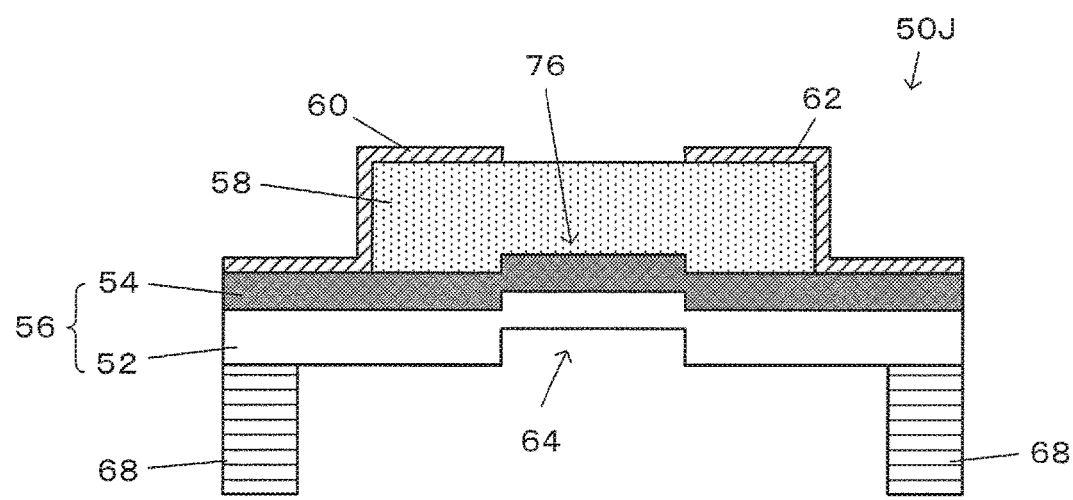
FIG. 17 is a diagram showing another configuration example of the piezoelectric element.

As shown in FIG. 17, a first projection portion 76 may be formed in a portion on one surface side (side on which the piezoelectric body 58 is disposed) of the vibrating film 56 corresponding to the first recess portion 64. For example, in the case of adopting a manufacturing step of forming the first recess portion 64 by pressure before providing the piezoelectric body 58 on the vibrating film 56, the first projection portion 76 is formed on a side opposite to the first recess portion 64 of the vibrating film 56. Such a configuration may be adopted.

Figure 18:
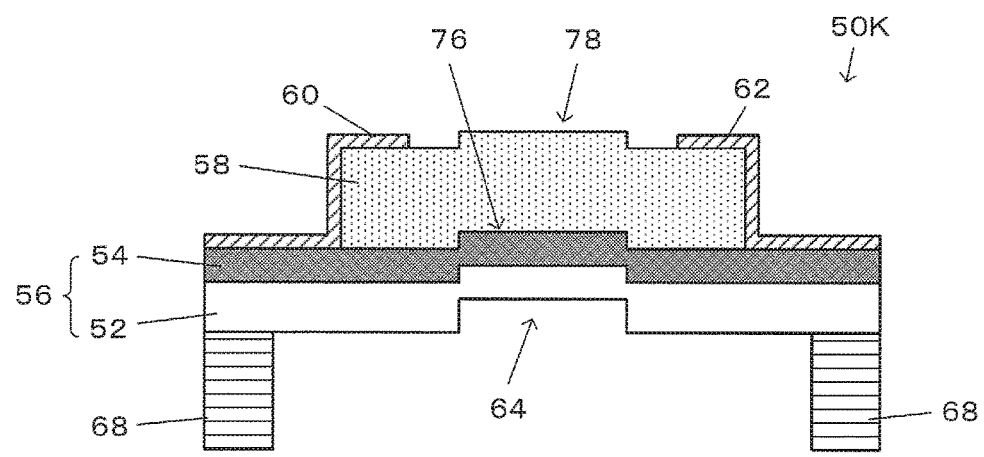
FIG. 18 is a diagram showing another configuration example of the piezoelectric element.

As shown in FIG. 18, a second projection portion 78 may be formed in a portion corresponding to the first recess portion 64 on the upper surface (surface on a side opposite to the surface on which the vibrating film 56 is disposed) of the piezoelectric body 58. For example, in the case of adopting a manufacturing step of forming the first recess portion 64 by pressure after providing the piezoelectric body 58 on the vibrating film 56, the same projection portion as in FIG. 17 is formed on a side opposite to the first recess portion 64 of the vibrating film 56, and the second projection portion 78 is further formed in a portion corresponding to the first recess portion 64 on the upper surface of the piezoelectric body 58. Such a configuration may be adopted.

Figure 19:
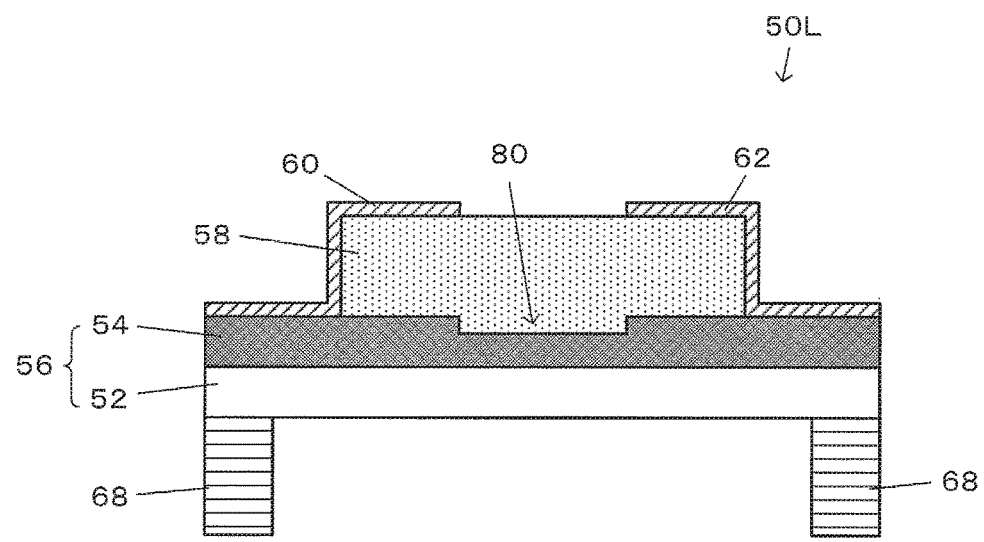
FIG. 19 is a diagram showing another configuration example of the piezoelectric element.

As shown in FIG. 19, a recess portion 80 may be formed in the zirconium oxide layer 54 on one surface side of the vibrating film 56. The Young's moduli of the zirconium oxide layer 54 and the piezoelectric body 58 are 200 GPa and 80 GPa, respectively. In a piezoelectric element 50L, compared with the piezoelectric element 50A shown in FIG. 7A, in an electrode gap portion, the thickness of the piezoelectric body 58 having a small Young's modulus is increased, and the thickness of the zirconium oxide layer 54 having a large Young's modulus is decreased. Through such a configuration, it is possible to form a structurally soft region in the electrode gap portion compared with the surrounding portion. Therefore, it is possible to concentrate distortion due to sound pressure on the electrode gap portion. As a result, it is possible to improve the reception sensitivity.

What is claimed is:

1. A piezoelectric element comprising:
a vibrating film;
a piezoelectric body disposed on one surface of the vibrating film; and
a horizontal electrode structure in which electrodes are disposed at a predetermined gap therebetween on the piezoelectric body and extend across an upper and side surface of the piezoelectric body such that the electrodes are disposed directly on the one surface of the vibrating film,
wherein the vibrating film includes a recess portion in a portion corresponding to the predetermined gap in plan view, and
wherein the recess portion is formed in a second surface of the vibrating film from the one surface of the vibrating film where the piezoelectric body is disposed.

2. The piezoelectric element according to claim 1, wherein a width of the recess portion along an electrode arrangement direction of the horizontal electrode structure is equal to or greater than the predetermined gap.

3. The piezoelectric element according to claim 1, wherein the predetermined gap is 2 μm or more and 8 μm or less.

4. The piezoelectric element according to claim 1, wherein, in the vibrating film, a boundary portion between the recess portion and a portion other than the recess portion is formed in a stepped shape, and a bottom surface of the recess portion is formed in a planar shape.

5. The piezoelectric element according to claim 1, wherein the recess portion is a groove extending in a direction crossing an electrode arrangement direction of the horizontal electrode structure.

6. The piezoelectric element according to claim 1, wherein the piezoelectric body includes a recess portion in a portion of the predetermined gap.

7. The piezoelectric element according to claim 5, wherein the piezoelectric body includes a groove-shaped recess portion, which is parallel to a groove direction of the recess portion of the vibrating film, in a portion of the predetermined gap.

8. The piezoelectric element according to claim 1, further comprising:
side wall portions that are provided with the recess portion of the vibrating film interposed therebetween for supporting the vibrating film,
wherein a width of the recess portion of the vibrating film is 0.3 times or more and 0.8 times or less of a distance between the side wall portions.

9. A piezoelectric element comprising:
a vibrating film;
a piezoelectric body disposed on one surface of the vibrating film; and
a horizontal electrode structure in which electrodes are disposed at a predetermined gap therebetween on the piezoelectric body and extend across an upper and side surface of the piezoelectric body such that the electrodes are disposed directly on the one surface of the vibrating film,
wherein the vibrating film includes a recess portion in a portion corresponding to the predetermined gap in plan view,
wherein in-plane distortion of the piezoelectric body is abruptly changed between a portion corresponding to the predetermined gap and a portion adjacent thereto in plan view, and in-plane distortion in the portion corresponding to the predetermined gap is larger than that in the portion adjacent to the portion corresponding to the predetermined gap, and
wherein the recess portion is formed in a second surface of the vibrating film from the one surface of the vibrating film where the piezoelectric body is disposed.

10. A probe for receiving an ultrasonic wave, comprising: the piezoelectric element according to claim 1.

11. A probe for receiving an ultrasonic wave, comprising: the piezoelectric element according to claim 2.

12. A probe for receiving an ultrasonic wave, comprising: the piezoelectric element according to claim 3.

13. A probe for receiving an ultrasonic wave, comprising: the piezoelectric element according to claim 4.

14. A probe for receiving an ultrasonic wave, comprising: the piezoelectric element according to claim 5.

15. A probe for receiving an ultrasonic wave, comprising: the piezoelectric element according to claim 9.

16. An ultrasonic measurement apparatus comprising the probe according to claim 10.

17. An ultrasonic measurement apparatus comprising the probe according to claim 11.

18. An ultrasonic measurement apparatus comprising the probe according to claim 12.

19. An ultrasonic measurement apparatus comprising the probe according to claim 13.

20. An ultrasonic measurement apparatus comprising the probe according to claim 15.

* * * * *